United States Patent [19]
Brattesani

[11] Patent Number: 5,743,431
[45] Date of Patent: Apr. 28, 1998

[54] FLUID DISPENSER AND ACTIVATOR ADAPTER AND METHOD OF USE

[76] Inventor: Steven J. Brattesani, 2561 Chestnut St., San Francisco, Calif. 94123

[21] Appl. No.: 683,057

[22] Filed: Jul. 16, 1996

Related U.S. Application Data

[63] Continuation-in-part of Ser. No. 543,176, Oct. 5, 1995, Pat. No. 5,692,642.

[51] Int. Cl.$^6$ .................................................. B67D 5/46
[52] U.S. Cl. .................. 222/1; 222/326; 222/327; 222/391; 433/90
[58] Field of Search ........................ 222/1, 326, 327, 222/174, 389, 390, 391; 604/209, 218, 228, 232–235; 433/89, 90

[56] References Cited

U.S. PATENT DOCUMENTS

| | | | |
|---|---|---|---|
| D. 357,536 | 4/1995 | Dragan et al. | |
| 3,110,310 | 11/1963 | Cislak | 604/209 |
| 3,141,583 | 7/1964 | Mapel et al. | 222/327 X |
| 3,319,839 | 5/1967 | Cox | 222/391 X |
| 3,726,440 | 4/1973 | Deeb | 222/327 X |
| 3,768,472 | 10/1973 | Hodosh et al. | 222/389 X |
| 4,099,548 | 7/1978 | Sturm et al. | 222/391 X |
| 4,264,305 | 4/1981 | Rasmussen et al. | 433/90 |
| 4,330,070 | 5/1982 | Doubleday | 222/326 X |
| 4,330,280 | 5/1982 | Dougherty et al. | |
| 4,360,332 | 11/1982 | Cyin | 222/389 X |
| 4,384,853 | 5/1983 | Welsh | |
| 4,444,560 | 4/1984 | Jacklich | 222/391 X |
| 4,472,141 | 9/1984 | Dragan | 433/90 |
| 4,738,664 | 4/1988 | Prindle | 604/228 |
| 5,015,233 | 5/1991 | McGough et al. | 222/389 X |
| 5,306,147 | 4/1994 | Dragan et al. | |
| 5,444,523 | 8/1995 | Fischer et al. | |

OTHER PUBLICATIONS

Miltex Aspirating Syringe "C–W" Type, IDE Interstate, Inc. Dental Supply Catalog, Fall 1994/Winter 1995, p. 12.
Miltex N–Tralig Intraligamental Anesthesia Syringe, Mitex Catalog #76–50, Undated.

*Primary Examiner*—Kevin P. Shaver
*Attorney, Agent, or Firm*—John P. O'Banion

[57] ABSTRACT

A dispenser adapter apparatus which allows activation and dispensing of multiple types of materials with use of a single dispensing device. The invention includes a cartridge holder with a socket for receiving a replaceable cartridge of adhesive, filler, or other material, and an activation chamber. The cartridge holder is reversibly coupled to a dispensing device such as a syringe or dispensing gun. The piston of the dispensing device applies an activating pressure to a cartridge within the activation chamber. The activated cartridge is transferred from the activation chamber to the socket. A plunger associated with the cartridge holder forces material from the cartridge. Force is transferred from the piston of the dispensing device to the plunger of the dispenser adapter apparatus by mechanically interfacing the piston and plunger.

20 Claims, 5 Drawing Sheets

FLUID DISPENSER AND ACTIVATOR ADAPTER AND METHOD OF USE

CROSS-REFERENCE TO RELATED APPLICATIONS

This application is a continuation-in-part of application Ser. No. 08/543,176 filed on Oct. 5, 1995, now U.S. Pat. No. 5,692, 642.

BACKGROUND OF THE INVENTION

1. Field of the Invention

This invention pertains generally to pressure actuated dispensers, applicators and devices for application of fluid materials, and more particularly, to an apparatus which provides for activating cartridges of adhesive or filler compound and for the application of such materials with conventional dispensing devices.

2. Description of the Background Art

A large variety of commercial and industrial fluid materials, such as adhesives, lubricants, fillers, sealants, caulking compounds, etchants, polishes, molding compounds and like materials are used in numerous applications. These fluid materials are generally viscous liquids which are typically available in disposable dispensers or dispensing devices or as disposable cartridges to be used with a dispensing device which accepts the cartridges. Some common examples of dispensing devices include "glue guns" for applying liquid adhesives and "grease guns" for applying liquid lubricants. Such dispensing devices generally utilize application of pressure, typically by a manually, pneumatically or hydraulically actuated plunger, onto a reservoir of fluid material to force the material out of the reservoir and through a nozzle, needle, applicator tip, or like exit means. The reservoir of fluid material may be an integral portion of the dispensing device, in which case the entire dispensing device is disposed of when the reservoir is depleted. More commonly, the reservoir of fluid material is contained in a cartridge, ampule, or capsule and, when the reservoir is depleted, the cartridge is removed from the device and replaced with a fresh cartridge.

An important drawback in currently used dispensing devices is that different dispensing devices are required for use with different types of fluid materials and for fluid materials from different commercial sources. Commonly used fluid materials vary in viscosity and chemical properties, and different dispenser devices are generally used for each type of material. For example, a "glue gun" is generally not structured and configured to dispense lubricants, and likewise a "grease gun" is generally not compatible with dispensing adhesives. Further, where multiple commercial sources exist for a particular fluid material available in cartridges, such as an adhesive or filler material, the different commercial sources generally provide different dispensing devices and cartridges which are not compatible with the cartridges or dispensing devices from other commercial sources. Thus, the users of such fluid materials must purchase multiple dispensing devices for the different types of fluid material used, and must purchase different dispensing devices for use with different commercial sources of the same material. This deficiency causes additional expense and adds to the cost of the goods and services ultimately produced.

The drawback of requiring multiple dispensing devices for multiple fluid materials and the multiple commercial sources therefor is perhaps most readily apparent in the dental and orthodontic professions, wherein a large number of liquid adhesive, filler, and other materials used for repair and restorative work are applied by various dispensing devices. Fluid materials such as glass ionomer compounds, resins, sealants, de-sensitizing agents, disinfecting agents, astringents, coagulants, chelating agents, amalgams, cements, porcelain cements, micro- and macro-fill composites and hybrid composites are used for numerous applications, including crowns, temporary and long-term fillings, bridgework, inlays, onlays, posts, pins, cast cores, cast crowns, orthodontic bands, and other applications. In endodontic dental applications, gutta percha or natural rubber is used as a filler for replacing the root or pulp material in root canal procedures. Also frequently used for dental and orthodontic applications are impression materials such as polyether, alginate, rubber, silicones, hydrocolloid, polysulfite and poly vinyl siloxane. All of the aforementioned materials are generally available as viscous fluids or extrudable pastes and compounds that are packaged in disposable capsules, ampules, cartridges, or "compules", which are generally dispensed through a tip applicator by means of special dispensing devices designed to receive a particular type or shape of cartridge. The dispensing devices are frequently pistol-like hand actuated dispensers which accept cartridges or capsules for a particular type and/or commercial brand of fluid material, and which apply pressure to cartridges by means of a plunger.

In the dental and orthodontic professions, the cost of the individual dispensing devices is fairly high, and the large variety of different materials used by dentists requires that a large number of different dispensing devices be purchased by each dental professional. The need for multiple dispensing devices results in additional expense and inconvenience to dentists and orthodontists and adds to the cost of patient treatment. The need for multiple dispensing devices additionally creates a clutter problem because numerous dispensing devices need to be on hand for each dental procedure.

Yet another problem associated with currently used dispensing devices in the dental and orthodontic professions is that the devices, which quickly become dirty or contaminated, are generally made of non-autoclavable materials and thus are difficult to clean and sterilize and must be frequently replaced, further increasing the ultimate cost of treatment. Further, the currently available devices which are autoclavable tend to degrade, break down or deteriorate through repeated sterilizations, and are prone to corrosion as well, and thus have life expectancies which are greatly reduced.

Many adhesive, filler and caulking fluid materials require activation or initiation prior to use. Such materials are usually dual component or multi-component materials, and typically comprise a polymerizable component or components and an initiator component or components. The polymerizable and initiator components are stored separately within the cartridge and are mixed just prior to use in order to activate the adhesive or filler material. When such materials are stored in cartridges as described above, the polymerizable components and initiator components are generally contained within the cartridge in one or more separate frangible containers or regions of the cartridge which are separated by frangible barriers. Prior to use of the adhesive or filler material, pressure is applied to the resilient exterior walls of the cartridge to break the internal frangible containers or barriers and cause mixing of the polymerizable component and initiator component, thereby activating the adhesive or filler. The activated mix is then dispensed or applied. Common examples of dual component materials which require activation prior to dispensation are the glass-ionomer adhesive and filler compounds used in the dental profession.

Currently used dispensing devices generally do not provide for the activation of fluid materials in cartridges prior to their dispensation. The users of such materials generally must activate the cartridges by hand or by an improvised hand-held tool, which is inconvenient, can damage the cartridges and render them unfit for use in the dispensing devices, or can result in incomplete activation of the material and result in non-optimum results in dental procedures and other applications.

Accordingly, there is a need for a fluid dispenser adapter apparatus and method which provides for the dispensing of many types of fluid materials from a single dispensing device, which provides for the activation of materials within cartridges, which is simple and inexpensive, which is autoclavable, which suffers less wear and tear and is not prone to degradation or corrosion, and which eliminates the need for purchasing and maintaining multiple syringe devices for use with different materials. The present invention satisfies these needs, as well as others, and generally overcomes the deficiencies found in the background art.

SUMMARY OF THE INVENTION

The present invention pertains to a fluid dispenser adapter apparatus and method which provides for the activation of cartridge-contained fluid materials such as pastes and gels, and for the dispensing or application of such materials from a single dispensing device. In its most general terms, the invention comprises a cartridge holder, a movable plunger associated with the cartridge holder, means for activating cartridge-contained materials, means for transferring force or pressure from a dispensing device to the plunger, and means for coupling the cartridge holder to a dispensing device.

By way of example and not of limitation, the cartridge holder or cartridge holding member includes a first end wherein a partially enclosed socket, receptacle, or recessed area is located for interchangeably receiving and holding cartridges of fluid material for dispensation. The structure and configuration of the socket or receptacle may be varied as required to accommodate various different sizes, shapes and types of cartridges or capsules for different types of fluid materials and cartridges from different commercial sources. Fluid material cartridges are reversibly received in the socket by means of snap fitting, frictional engagement, bayonet mounting, or like means. A longitudinal bore in the cartridge holder communicates with the socket and slidably accommodates the plunger. A first end of the plunger is preferably structured and configured to apply pressure on a reservoir portion of a cartridge held in the socket of the cartridge holder.

The means for transferring pressure from a dispensing device to the plunger is generally associated with a second end of the plunger. In its simplest form, the transferring means may comprise a flat surface on the second end of the plunger which is structured and configured to receive pressure applied by a piston or other pressure-applying member associated with a standard dispensing device. Alternatively, a shank may be included at the second end of the plunger, and the transferring means may comprise a flat surface on the shank. The transferring means may alternatively comprise other structural features associated with the second end of the plunger which facilitate transfer of force or pressure from the piston of the dispensing device to the plunger. Means for retaining the plunger within the bore of the cartridge holder may also be included with the invention.

The means for coupling the cartridge holder to a dispensing device is preferably associated with a second end of the cartridge holder, and may comprise an externally threaded portion for attachment to a dispensing device. The coupling means may also comprise a bayonet mounting arrangement or other quick release arrangement for quick and facile interchanging of dispenser adapters on a dispensing device. Snap-fitting type coupling means, frictional coupling means, and other conventional coupling means are also contemplated for use with the invention.

The activation means preferably comprises an activation chamber or receptacle which is generally associated with the cartridge holder, preferably adjacent the second end thereof. An opening in the chamber allows insertion and removal of cartridges from the chamber. Means for applying activating pressure to a cartridge by a dispensing device are associated with the chamber, preferably in the form of an aperture or opening in the chamber adjacent the coupling means which allows access to the chamber by a piston of a dispensing device. The bore in the cartridge holder communicates with the activation chamber, and the plunger and transferring means are preferably located on a side or end of the activation chamber opposite to the opening and coupling means. The activation chamber is preferably structured and configured so that the piston of the dispensing device applies pressure to a side of the cartridge while a cartridge is contained therein. The size and shape of the activation chamber may be varied as required to accommodate a variety of different cartridge configurations.

A conventional dispensing device which generally can only dispense or apply material from a single type or shape of cartridge, may be modified by attachment of the dispenser adapter of the invention to allow different types of cartridges, and thus different fluid materials from different commercial sources, to be activated and dispensed with the same conventional dispensing device. Different dispenser adapters, wherein the cartridge holder and activation chamber of each different dispenser adapter are structured and configured to receive different sizes and shapes of cartridge, provide for activation and dispensing of multiple materials from multiple commercial sources with a single dispensing device. The length and shape of the dispenser adapter may be varied as required for different applications. Activation and dispensing of large or small volume cartridges may be carried out with the same dispensing device by use of different dispenser adapters with the dispensing device. Since the dispenser adapter comprising the invention is simple and inexpensive to manufacture, the use of multiple dispenser adapters with a single standard dispensing device provides a substantial commercial benefit over the use of multiple dispensing devices. The position and orientation of the cartridge while dispensing material therefrom may be adjusted by turning or rotating the cartridge holder relative to the dispensing device, allowing greater accuracy in applying fluid materials. Currently available dispensing devices, in contrast, hold fluid material cartridges which are locked in place and do not allow the accuracy in application obtainable with the present invention.

The method of utilizing the present invention, in general terms, comprises the steps of coupling a dispenser adapter to a dispensing device, activating the fluid material within the cartridge by applying force thereto with the coupled dispensing device, transferring the cartridge of activated material from the activation chamber to the socket of the cartridge holder, transferring pressure from the dispensing device to the plunger of the dispenser adapter, and forcing fluid material from a cartridge in the dispenser adapter by means of the plunger. The steps of inserting a cartridge of fluid material into the activation chamber of the dispenser adapter, removing the activated capsules from the activation chamber, and the repeating of the above steps, are also generally included with the invention.

The method of using the invention is generally carried out by coupling the dispenser adapter onto a standard dispensing device in a position such that pressure from the dispensing device may be transferred to the activation chamber and to the plunger associated with the cartridge holder of the invention. For dispensing devices wherein manually or hydraulically actuated pistons are involved, the dispenser adapter is generally coupled to the dispensing device in a manner such that the piston of the dispensing device can enter the activation chamber and interface mechanically with the plunger of the dispenser adapter. A cartridge of fluid material is then inserted into the activation chamber, and pressure is applied to the resilient sides or walls of the cartridge by the piston of the dispensing device to mix and activate the fluid materials therein. The piston enters the activation chamber through the aperture communicating with the activation chamber. The pressure applied to the cartridge while in the activation chamber is such that the contents of the cartridge are activated without rupturing or breaking the walls of the cartridge. The activated cartridge is then removed from the activation chamber and inserted into the socket of the cartridge holder and positioned so that pressure from the plunger may be applied to a rear or back end of the cartridge to empty or dispense the fluid contents from the cartridge. A replaceable tip applicator may be included on the cartridge holder to facilitate dispensing of materials with the dispenser adapter. When the plunger has forced all of the fluid material out of the cartridge, the empty cartridge is removed and a fresh cartridge is activated and used in the same manner. A different fluid material may be activated and dispensed from the dispensing device by uncoupling the dispenser adapter from the dispensing device, and attaching a different dispenser adapter which is structured and configured to accommodate cartridges of the different material.

The parts of the invention may be made of autoclavable, corrosion-resistant metal and/or polymeric material to provide long service lifetime even with repeated autoclaving. The invention may alternatively be fabricated from inexpensive polymeric material and used as a disposable apparatus. The cartridge holder and plunger of the invention may also be fabricated from flexible or resilient polymeric materials to allow bending or twisting of the apparatus for more accurate application of fluid materials. An anti-slip coating or surface may be included on the dispenser adapter to allow users to handle the invention while wearing latex gloves. An anti-stick coating may be included on the plunger and cartridge holder of the invention to prevent adhesives and other sticky materials from causing the plunger to jam, which is a drawback present in currently available dispensing devices. Since the invention is simple to use and is utilized with conventional dispensing devices, persons using the invention will not need to become familiar with a large number of different types of dispensing devices.

The dispenser adapter comprising the invention may be employed in dental, orthodontic, medical, veterinary, and other clinical and laboratory fields by utilizing conventional syringe devices such as aspirating or intraligamental anesthetic syringes which are typically possessed by persons in the above professions. The invention is thus employed by removing the needle from the end of the syringe, and coupling the cartridge holder thereon. A cartridge is placed within the activation chamber, and pressure is applied to the side or walls of the cartridge by the piston of the syringe to mix and activate the fluid materials contained in the cartridge. The activated cartridge is then removed from the activation chamber, and engaged within the socket of the cartridge holder, preferably by snap fitting or other standard means, and a tip applicator is attached to the cartridge (if required). Then, the material within the cartridge is dispensed by manually actuating the syringe piston in a standard manner to apply pressure to the rear or back end of the cartridge. Different dispenser adapters may be used to accommodate different types of material capsules or cartridges with the same syringe, thereby eliminating the need for multiple syringe devices for dispensing different types and commercial sources of materials used in the aforementioned professions.

An object of the invention is to provide a dispenser adapter which allows the dispensing of multiple fluid materials from a single dispensing device.

Another object of the invention is to provide a dispenser adapter which allows for activation, initiation, or mixing of fluid materials within cartridges.

Another object of the invention is to provide a dispenser adapter which is easily interchangeable.

Another object of the invention is to provide a dispenser adapter which allows dispensing of fluid materials from multiple commercial sources.

Another object of the invention is to provide a dispenser adapter which is autoclavable and reusable.

Another object of the invention is to provide a dispenser adapter which is simple and easy to use.

Another object of the invention is to provide a dispenser adapter which has few moving parts and thus is not susceptible to breakage and does not require repair.

Another object of the invention is to provide a dispenser adapter which eliminates the clutter associated with use of multiple dispensing devices for a single operation or procedure.

Another object of the invention is to provide a dispenser adapter which is resistant to wear, deterioration, degradation and corrosion.

Another object of the invention is to provide a dispenser adapter which may be fabricated from inexpensive materials to provide a disposable apparatus.

Another object of the invention is to provide a dispenser adapter which allows application of materials in multiple directions through turning or rotation of a cartridge holder.

Another object of the invention is to provide a dispenser adapter which provides for multiple lengths to allow precision application of fluid materials.

Another object of the invention is to provide a dispenser adapter which may be fabricated from flexible or resilient polymeric material to allow increased accuracy in applying fluid materials.

Further objects of the invention will be brought out in the following portions of the specification, wherein the detailed description is for the purpose of fully disclosing the invention without placing limits thereon.

BRIEF DESCRIPTION OF THE DRAWINGS

The invention will be more fully understood by reference to the following drawings which are for illustrative purposes only.

DESCRIPTION OF THE PREFERRED EMBODIMENTS

Figure 6:
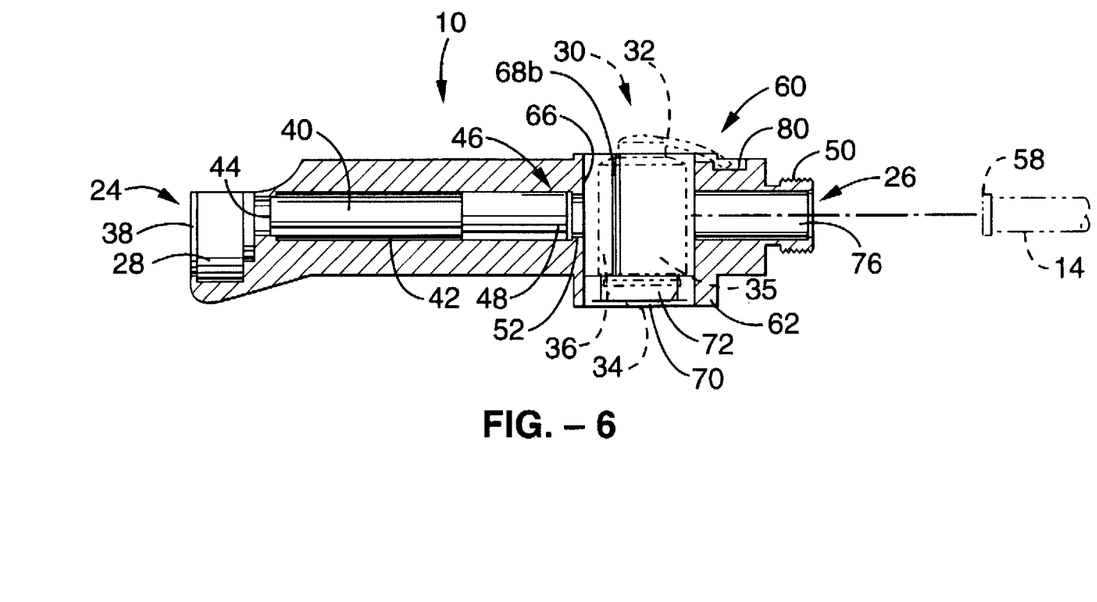
FIG. 6 is a perspective view of the dispenser adapter shown in FIG. 1 through FIG. 5 showing a cartridge within the activation chamber.
Figure 7:
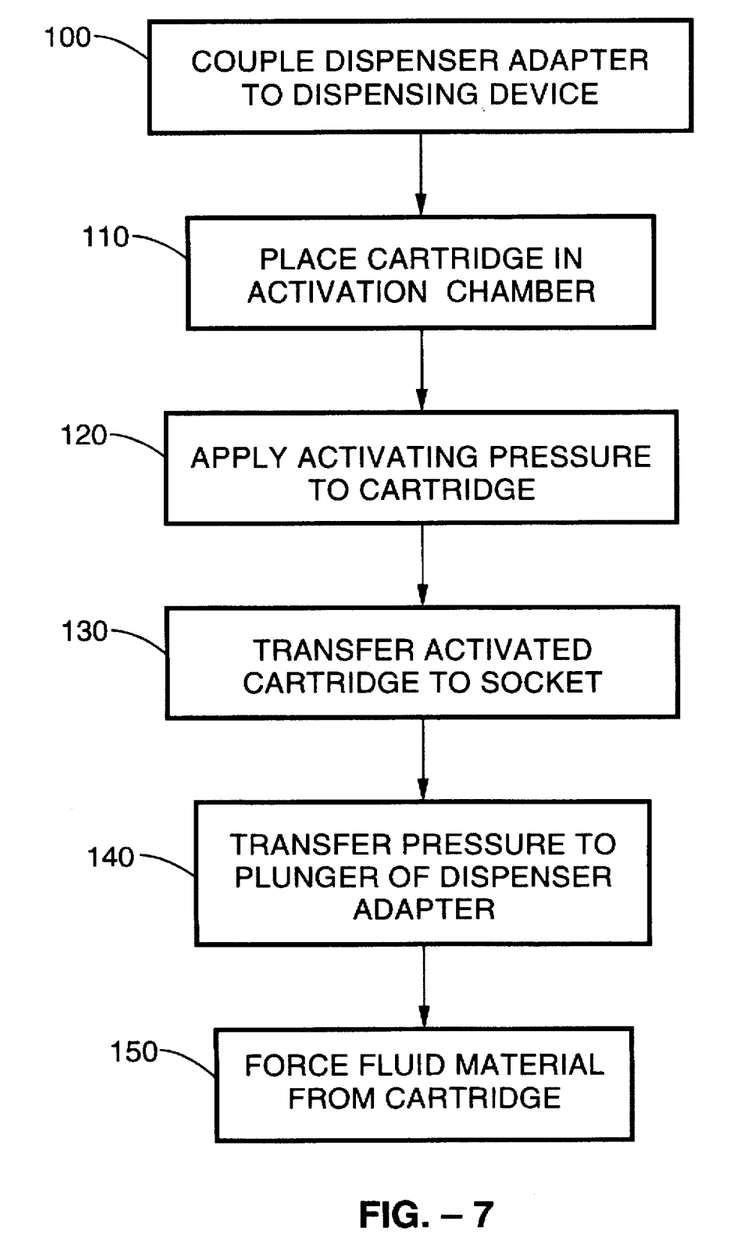
FIG. 7 is a diagram showing generally the steps of the method of using the invention.

Referring more specifically to the drawings, for illustrative purposes the present invention is embodied in the apparatus which is generally shown in FIG. 1 through FIG. 6, and the method which is generally shown in FIG. 7. It will be appreciated that the apparatus may vary as to configuration and as to details of parts, and that the method may vary as to the steps and their sequence, without departing from the basic concepts as disclosed herein. Thus, the following detailed description is merely exemplary, and should not be considered limiting.

For reasons of clarity, the present invention is described in this disclosure in terms of use with hand-actuated, syringe-type dispensing devices as are commonly utilized in dental, medical, veterinary, clinical, and laboratory applications, and the use of the invention is related generally in terms of dental applications. However, as should be readily apparent to persons of ordinary skill in the art, the dispenser adapter of the present invention may be used with a large variety of dispensing devices in a number of applications. Thus, the term "dispensing device" as used herein means generally any device wherein pressure-actuated dispensation of fluid materials is carried out. The dispensing devices suitable for use with the present invention generally will comprise a manually actuated piston or plunger which applies force or pressure. However, dispensing devices which apply force by hydraulic, pneumatic and other means may also be used with the invention. The term "fluid material" as used herein refers generally to all types of liquids, pastes, gels, slurries, powders and like materials which may be dispensed, applied, squeezed or extruded through a nozzle or applicator by application of pressure. The drawings of this disclosure generally show the invention with a particular cartridge or compule configuration which is commonly used for glass-ionomer compounds in the dental profession. Those skilled in the art will recognize, however, that the particular cartridge as illustrated herein is merely exemplary, and is only one of many possible cartridge structures and configurations which may be used with the invention.

The invention is particularly well suited for use with cartridge-contained materials which require activation or initiation prior to use. Many common adhesive and filler fluid materials are dual or multi-component materials which must be mixed together within the cartridge prior to use. The individual components of such fluid mixes may comprise, for example, one or more polymerizable materials such as monomers or oligomers which are polymerizable by free-radical, cationic, anionic, thermal, or other types of catalyst-initiated polymerization. The individual components of such fluid materials also generally comprise one or more initiator materials such as alkyl or aryl peroxides or azo compounds, amines, or other polymerization initiators or catalysts. As mentioned above, the individual components are stored separately within cartridges by means of separate frangible containers or by frangible barriers within the cartridges. Activation is achieved, as described in detail below, by applying pressure to flexible outer walls of the cartridge to break the frangible containers or barriers and mix the polymerizable component or components with the initiator component or components, thereby activating the fluid material. Background art dispensing devices do not provide for activation of materials within cartridges, and the present invention remedies this deficiency.

Figure 1:
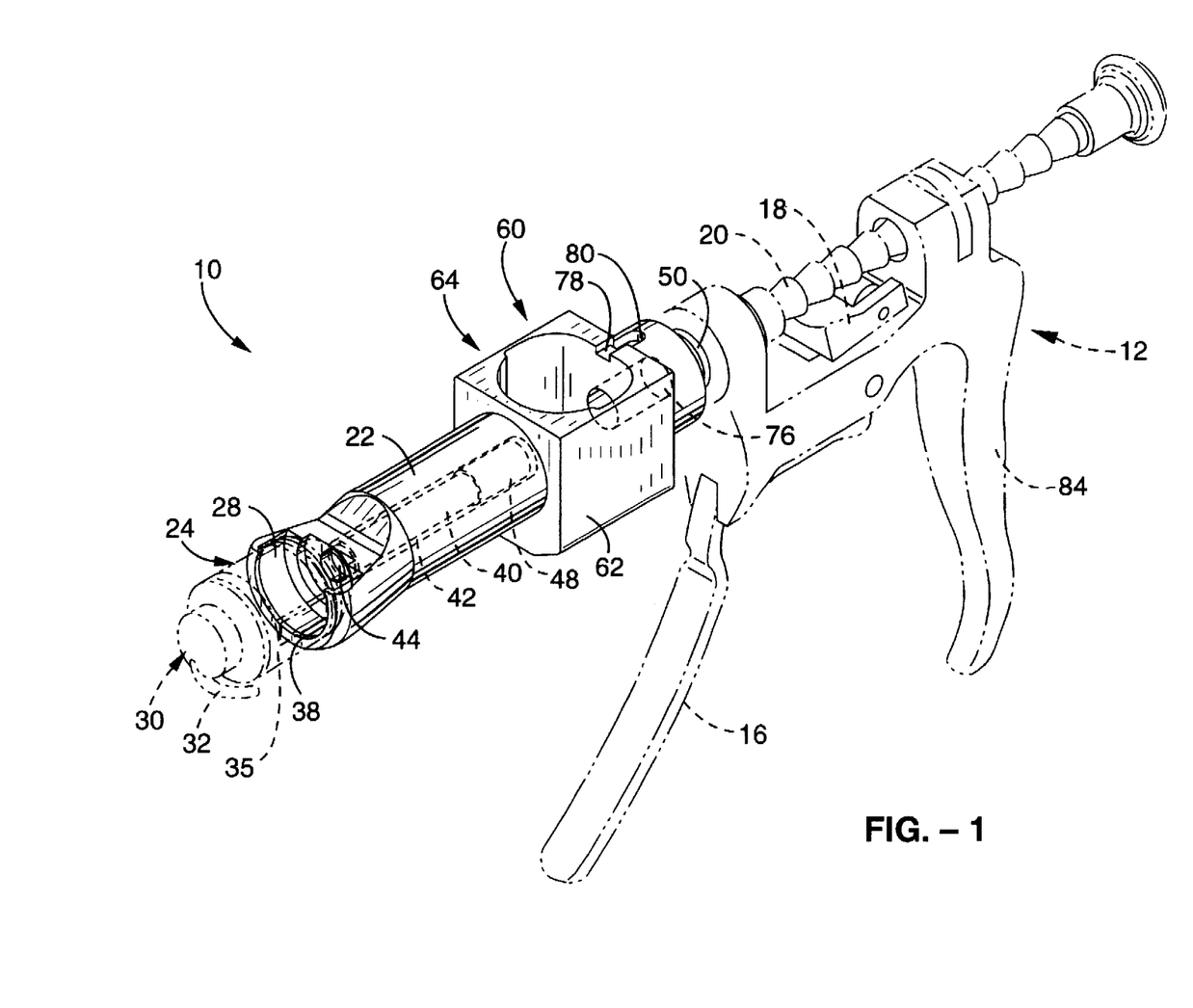
FIG. 1 is a perspective view of a dispenser adapter in accordance with the present invention, coupled to a conventional pistol-type dispensing device and a replaceable cartridge shown in phantom.
Figure 2:
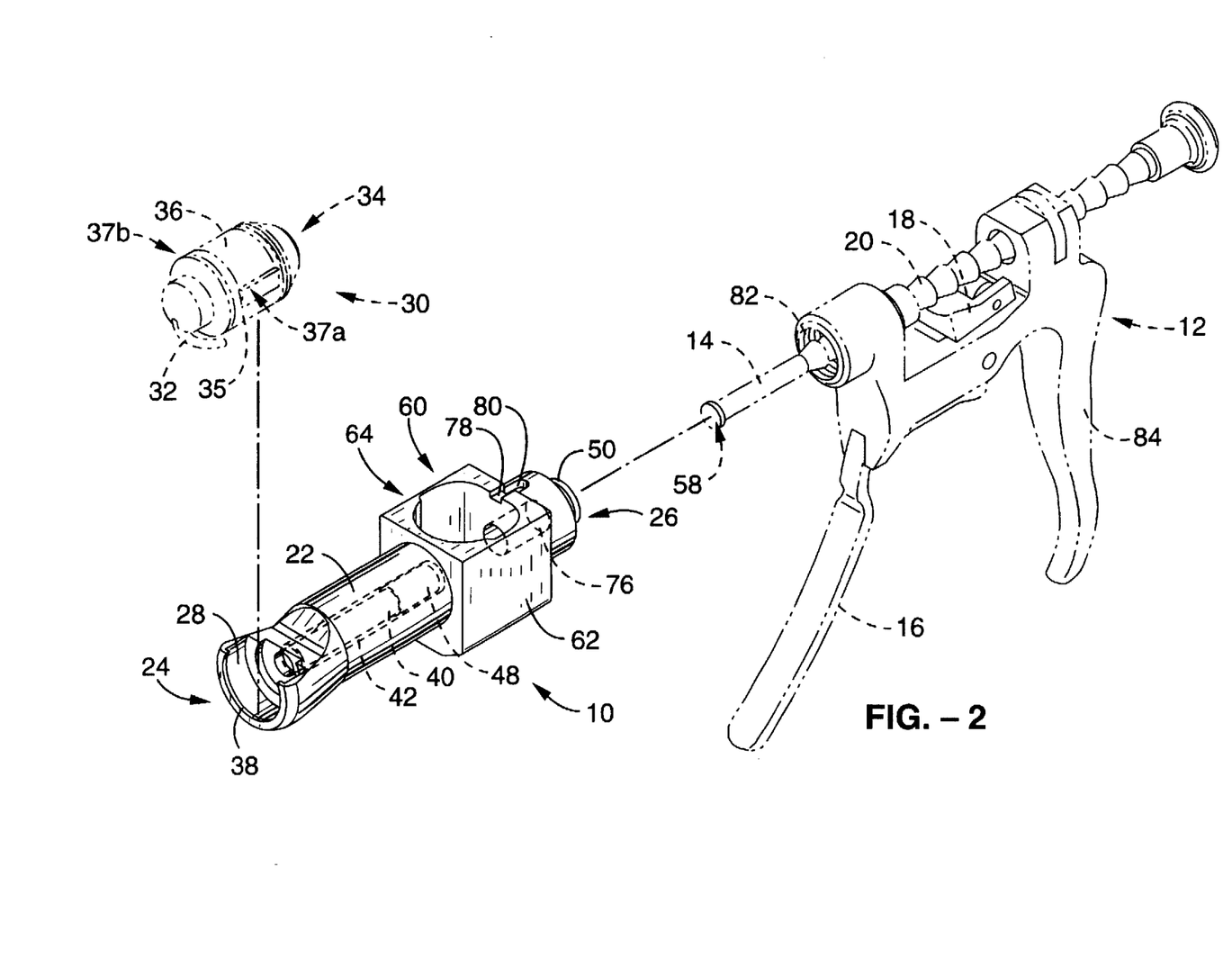
FIG. 2 is an exploded view of the assembly shown in FIG. 1.

Referring first to FIG. 1 through FIG. 6, there is shown generally a dispenser adapter 10 in accordance with the present invention, coupled to a conventional pistol-type dispensing device 12 shown in phantom. Dispensing device 12, which is merely one of a variety of types of dispensing devices contemplated for use with the present invention, operates in a standard fashion wherein a piston 14 (FIG. 2) is incrementally advanced by means of a ratchet and pawl mechanism. Actuation of trigger 16 on dispensing device 12 mechanically actuates pawl 18 by conventional means, allowing piston 14 to move in increments defined generally by sloped notches 20 along piston 14. The dispensing device 12 shown in FIG. 1 and FIG. 2 is typical of those commercially available from the Miltex Company for use as an intraligamental syringe. Similar dispensing devices may be obtained from several sources. A conventional aspirating syringe or other dispensing device may also be used with the invention.

Dispenser adapter 10 comprises a cartridge holder or cartridge holding member 22 having a first end 24 and a second end 26. A partially enclosed dispensing socket, receptacle or recessed area 28 adjacent first end 24 defines an opening that is structured and configured to detachably receive an interchangeable and replaceable capsule, ampule, compule, or cartridge 30 which contains fluid material to be dispensed. Cartridge 30 as shown is a standard configuration for glass-ionomer compounds used in the dental profession, with cartridge 30 including an applicator tip 32, a rear or back end 34, and a resilient or flexible cylindrical shell or sidewall 35. A jacket 36 partially encircles shell 35 of cartridge, and a pair of ridges 37a, 37b extend along the edges of jacket 36. A frangible pocket (not shown) is generally included between jacket 36 and shell 35, as discussed further below. Cartridge 30 is shown in a standard arrangement with applicator tip 32 angled toward the side of cartridge 30. In other commonly used cartridge configurations (not shown) which may be used with the invention, applicator tip 32 extends generally straight forward from the front of the cartridge 30. Socket 28 opens up towards the side of cartridge holder 22 as well as toward first end 24 of cartridge holder 22 to facilitate interchanging of cartridges 30. Socket 28 of cartridge holder 22 preferably engages cartridge 30 by friction, snap fitting, bayonet mounting or other conventional means, and is retained therein during dispensation of materials. Socket 28 and cartridge holder 22 preferably are of rigid, non-flexible construction relative to the flexible shell 35 of cartridge 30, and thus snap fitting is provided by the resilient nature of the shell 35 of cartridge 30. A partially encircling lip or flange 38 helps retain cartridge 30 within socket 28.

As related above, different types of fluid materials, such as adhesives, lubricants, sealants, and fillers are generally available in cartridges of different sizes and shapes, and different commercial sources for such materials tend to provide cartridges in varying sizes and shapes. Cartridge 30 as shown is merely one type of cartridge or compule which may be used with the invention. Various additional cartridge structures and configurations may be used with the invention. For example, other common cartridge configuration (not shown) used in the dental profession are narrower and longer than cartridge 30, and frequently have a bullet or torpedo shaped structure. Accordingly, the size and shape of cavity or socket 28 and cartridge holder 22 may be varied in order to accommodate any type of cartridge. Socket 28 of cartridge holder 22 is shown in a preferred structure and configuration for receiving standard compules or cartridges 30 of dual component or multi-component adhesive and filler compounds such as glass-ionomer compounds which are commonly used in the dental profession. The length and shape of cartridge holder 22 may be also be varied to accommodate particular dispensing operations. For example, a longer, barrel shaped cartridge holder 22 may be used for posterior dental applications, while a shorter cartridge holder may be used for anterior dental applications, as discussed further below.

The present invention also comprises a plunger or rod 40 associated with cartridge holder 22. Preferably, a longitudinal bore 42 in cartridge holder 22 slidably accommodates plunger 40. Plunger 40 is preferably elongated in shape and of generally cylindrical structure and configuration, although a variety of plunger shapes and configurations are suitable for use with the invention. Plunger 40 includes a first end 44 and a second end 46 (FIG. 4), with the first end 44 of plunger 40 generally adjacent to socket 28 in cartridge holder 22. A shank portion 48 may be included on plunger 40 adjacent second end 46. First end 44 of plunger 40 is generally structured and configured to apply pressure to back end 34 of cartridge 30 during extension so that the fluid material contained therein is discharged from the cartridge 30, as described further below.

Means for coupling cartridge holder 22 to a dispensing device are also included with the invention. Preferably, the coupling means comprises a threaded portion 50 adjacent second end 26 of cartridge holder 22. Threaded portion 50, while shown as externally threaded, may be internally threaded or otherwise suitably structured and configured for coupling to a conventional dispensing device such as dispensing device 12. The coupling means could alternatively comprise a snap fitting arrangement, frictional means, bayonet mounting, conventional quick release fittings, or any other coupling means commonly used in the art. Threaded portion 50 may itself be detachable from cartridge holder 52 and interchangeable, so that the coupling means of the invention may be interchanged, allowing attachment of the same dispenser adapter apparatus 10 to a variety of dispensing devices.

Figures 3, 4:
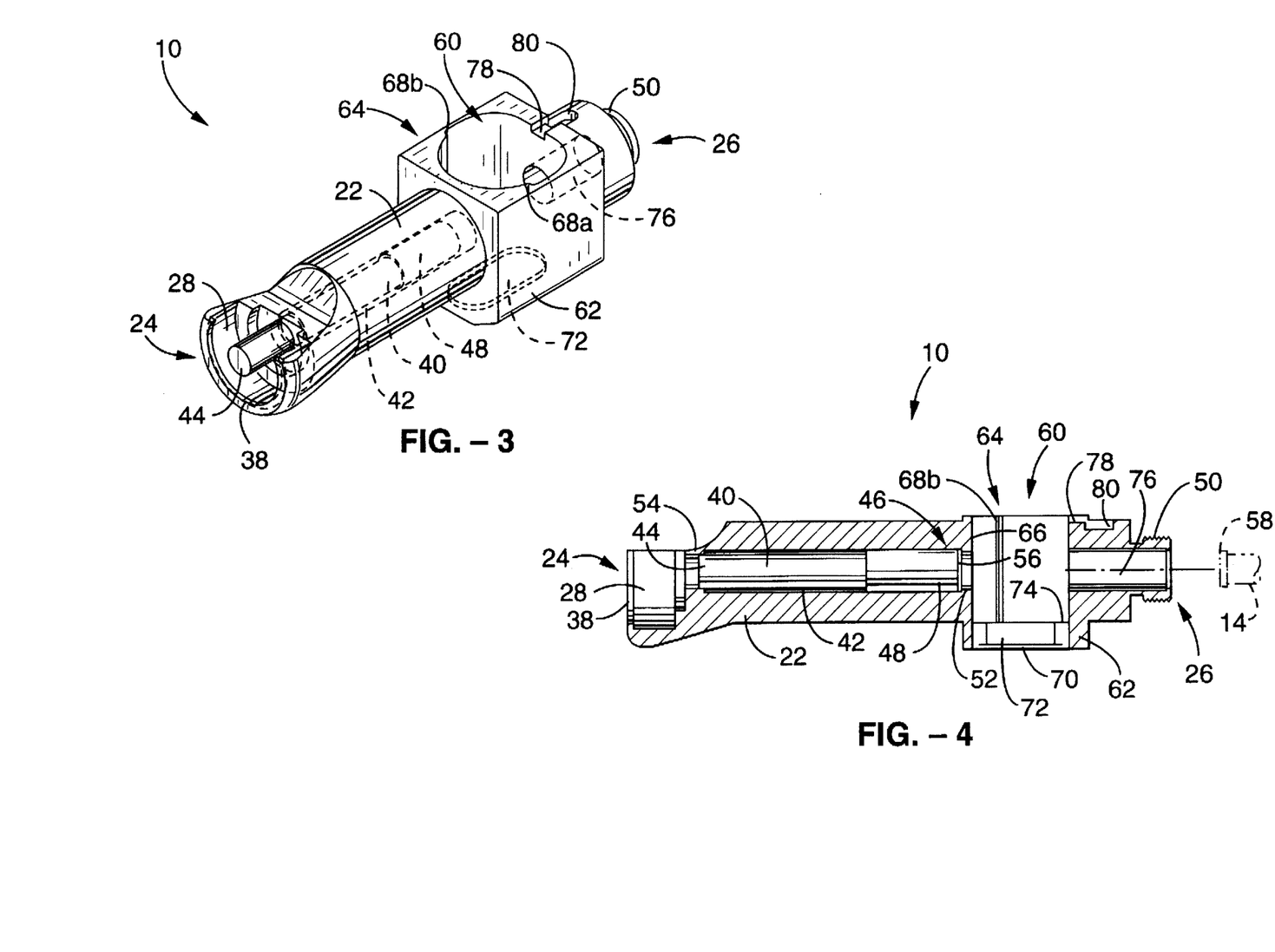
FIG. 3 is a perspective view of the dispenser adapter of FIG. 1 and FIG. 2 showing the plunger in an extended or forward position.
FIG. 4 is a cross-sectional view of the dispenser adapter of FIG. 3 taken through line 4—4, and showing the plunger in a retracted position.
Figure 5:
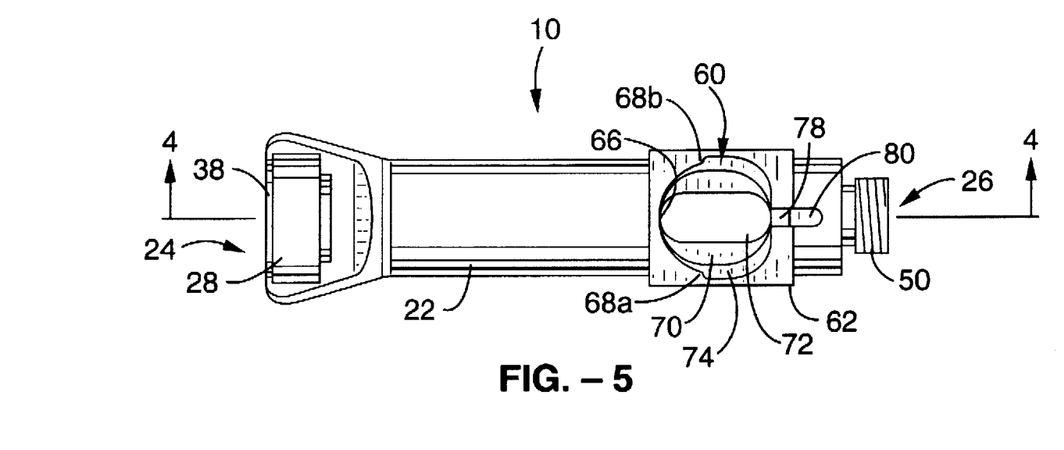
FIG. 5 is a top plan view of the dispenser adapter shown in FIG. 1 through FIG. 4.

Means for retaining plunger 40 in bore 42 of cartridge holder 22 may be included with the invention, to prevent loss of plunger 40 during cleaning and otherwise minimize inconvenience. As shown in FIG. 4, the retaining means preferably comprises an inwardly disposed lip 52 within bore 42, and an inwardly disposed lip or shoulder 54 within bore 42 adjacent socket 28, which prevent shank portion 48 on plunger 40 from disengaging or sliding out of bore 42.

Also provided with the invention are means for transferring force or pressure from a dispensing device to the plunger 40 of dispenser apparatus 10. The transferring means, as shown in FIG. 4 and FIG. 6, preferably comprises a flat surface 56 on shank portion 48 which is structured and configured to interface with a flat end 58 on piston 14 of dispensing device 12. The transferring means employed with the invention, however, will generally vary with the types of dispensing devices utilized with the invention. For example, use of the invention with dispensing devices having pistons which do not include a flat end will generally require different means for interfacing with the piston of the dispensing device.

The invention includes means for activating fluid materials contained in cartridge 30. The activating means preferably comprises an activation chamber or receptacle 60 included in cartridge holder 22, preferably adjacent to second end 26 and coupling means 50. Activation chamber 60 is contained in a housing 62 which is preferably integral to cartridge holder 22. A laterally facing opening 64 in housing 62 allows insertion and removal of cartridge 30 from activation chamber 60. Activation chamber 60 may be structured and configured as required to accommodate various sizes and shapes of cartridge 30. As with socket 28, activation chamber 60 is shown as structured and configured to receive standard, commercially available cartridges of glass ionomer compound of the type commonly used in the dental profession. Activation chamber 60 includes a curved or arcuate front wall 66 which is structured and configured to partially receive jacket 36 of cartridge 30. A pair of shoulders 68a, 68b are provided on arcuate front 66 to accommodate ridges 37a, 37b on jacket 36 of cartridge 30. Activation chamber 60 has a generally flat bottom 70, with an opening or slot 72 in bottom 70 which communicates with the exterior of housing 62. Slot 72 is structured and configured to receive back end 34 of cartridge 30 when cartridge 30 is in activation chamber 60. A shelf or ledge 74 is also included in activation chamber 60 adjacent bottom 70 to accommodate cartridge 30. Bore 42 communicates with activation chamber 60, and lip 52 within bore 42 is preferably positioned adjacent activation chamber 60.

Means for applying activating pressure to a cartridge by a dispensing device are associated with activation chamber 60, preferably in the form of an aperture or bore 76 adjacent second end 26 and threaded portion 50 and opposite to bore 42 and second end 46 of plunger 40. Aperture 76 extends through threaded portion 50 into activation chamber 60 and allows access to activation chamber 60 by piston 14 of dispensing device 12 to apply activating pressure to a cartridge 30, as discussed further below. Aperture 76 is preferably co-linear with bore 42 which contains plunger 40, and is structured and configured to slidably receive or accommodate piston 14 on dispensing device 12. The structure and configuration of aperture 76 may be varied to accommodate pistons of different dimensions.

Cartridge 30 is shown with a curved applicator tip 32, which is one common configuration for cartridges used in the dental profession for glass-ionomer compounds. A groove 78 in cylindrical housing 62, together with a recessed portion 80 in cartridge holder 22, are provided for use with cartridges 30 having a curved applicator tip 32, so that applicator tip 32 is not bent or otherwise damaged while cartridge 30 is inserted within activation chamber 60, as shown in FIG. 6. As related above, different cartridge configurations have varying applicator tip shapes and configurations, and other structural features, such as suitably placed notches, slots, shoulders, corners, shelves, ledges, or recesses, may be included on cartridge holder 22 to accommodate varying applicator tip structures.

The dispenser adapter 10 is utilized generally by coupling the cartridge holder 22 to dispensing device 12 by engaging threaded portion 50 with an internally threaded socket 82 (FIG. 2) on dispensing device 12, with piston 14 adjacent aperture 76. Traction means, such as a plurality of longitudinal ridges or serrations (not shown) may be included on cartridge holder 22 to facilitate handling. Referring more particularly to FIG. 6, a cartridge 30 is placed within activation chamber 60, with back end 34 of cartridge 30 positioned within slot 72 in the bottom 70 of activation chamber 60, with jacket 36 adjacent arcuate front wall 66, with ridges 37a, 37b on jacket 36 adjacent shoulders 68a, 68b, and with the unjacketed portion of shell or side wall 35 positioned adjacent aperture 76. Groove 78 and recessed area 80 accommodate curved applicator tip 32. A user then grasps handle grip 84 on dispensing device 12, and actuates trigger 16 by applying force or pressure thereto, thereby moving or advancing piston 14 incrementally forward. The end 58 of piston 14 extends through aperture 76 into activation chamber 60 and contacts and applies activating pressure to the resilient shell 35 of cartridge 30. A frangible packet or pocket (not shown) containing a component of the material to be dispense is included between jacket 36 and side wall 35. As activating pressure is applied to side wall, side wall 35 is pressed into jacket 36, causing the frangible pocket to rupture. Jacket 36 is held in a substantially stationary position against front wall 66 by the interaction of ridges 37a, 37b on jacket 36 with shoulders 68a, 68b on front wall 66, to facilitate the rupturing of the frangible pocket upon application of pressure by piston 14. The contents of the ruptured packet are forced through an opening (not shown) in side wall 35 and into the interior of cartridge 30 wherein the contents of the frangible packet are mixed with the other component(s) of the fluid material therein to be dispensed. Back end 34 of cartridge 30, which may be frangible to facilitate dispensing fluid materials as discussed below, is held within slot 72 in the bottom 70 of activation chamber 60 and thus protected from receiving pressure from piston 14 during activation.

In other cartridge configurations, activating pressure applied by piston 14 to cartridge 30 may cause rupturing or breaking of frangible barriers or containers (not shown) which are internal to side wall 35, rather than external thereto and held between the side wall 35 and jacket 36. In general, the application of activating pressure exposes the polymerizable component of the fluid material in cartridge 30 to the initiator component, as described above, to activate the fluid material. Flexible shell 35 of cartridge 30 preferably is sufficiently robust so that the pressure required for activation of the fluid material does not rupture or damage shell 35.

The thusly activated cartridge 30 is then removed from activation chamber 60 and placed into socket 28 and securely engaged therein by friction, snap fitting, or other means. Cartridge 30 is placed within socket 28 such that back end 34 is adjacent first end 44 of plunger 40. The user then actuates trigger 16 by applying force or pressure thereto, moving or advancing piston 14 incrementally forward. Piston 14 extends through activation chamber 60 into bore 42, and flat end 58 of piston 14 contacts flat surface 56 on second end 46 of plunger 40. With piston 14 and plunger 40 thus mechanically interfaced by contact of flat end 58 of plunger and flat surface 56 on shank portion 48 of plunger 40, force or pressure is transferred to plunger 40 from piston 14, and plunger 40 slides or otherwise moves forward within bore 42 towards cartridge 30 as piston 14 moves forward. The pressure applied by first end 44 of plunger 40 on back end 34 of cartridge 30 forces the fluid material out of cartridge 30 and through tip applicator 32. Plunger 40 generally penetrates frangible back end 34 of cartridge 30 and proceeds through cartridge 30 while forcing the discharge of materials therefrom. When cartridge 30 is spent or empty, piston 14 on dispensing device 12 is retracted, plunger 40 is disengaged from cartridge 30, the spent cartridge removed from socket 28 and a fresh cartridge placed in activation chamber 60, and the above procedure is repeated.

If the user wishes to use dispensing device 12 for activating and dispensing another type of material in a different type of cartridge or a cartridge having a different structure and configuration, then the dispenser adapter 10 is disengaged from dispensing device 12, and another dispenser adapter which is suitably structured and configured for the different cartridge is coupled to the dispensing device 12 and used in generally the same manner. If the user wishes to dispense fluid materials which do not require activation, the cartridge 30 is placed directly into socket 28 of cartridge holder as described above, without use of the activation chamber 60. In such a case, piston 14 of dispensing device 12 is advanced through aperture 68 and activation chamber 60 until flat end 58 of piston 14 interfaces flat end 56 on plunger 40.

The method of using the invention will be seen more clearly by reference to FIG. 7, wherein a flow chart generally outlining the steps of using the invention is shown, as well as FIG. 1 through FIG. 6. In step 100, a dispenser adapter apparatus 10 is coupled to a conventional dispensing device such as the pistol-type or syringe-type dispensing device 12 described above. The coupling may be carried out by means of interfitting threaded portions 50, 82 as described above, or by snap fitting, frictional engagement, or any other standard coupling means.

In step 110, a cartridge 30 is inserted into an activation chamber 60 associated with a cartridge holder 22 on the dispenser adapter apparatus 10. Generally, the cartridge 30 is inserted within the activation chamber in a position such that the frangible back end 34 of the cartridge 30 will not be exposed to activating pressure in a subsequent step. Preferably, a slot 72 is provided in the bottom 70 of activation chamber 60 to protect back end 34 of cartridge 30 during activation, as described above. The cartridge 30 is positioned within the activation chamber 60 so that subsequent activating pressure may be applied to the resilient side wall 35 of the cartridge 30, as is also described above.

In step 120, activating pressure is applied by the dispensing device 12 to the cartridge 30 in the activation chamber 60 of the dispenser adapter apparatus 12, to activate the fluid material contained within the cartridge. As described above, the individual components of the fluid material are generally stored separately within the cartridge 30, and activating pressure is provided by the piston of the dispensing device to the flexible shell 35 of the cartridge 30 in the activation chamber 60 to break frangible containers or barriers within the cartridge and mix the components of the fluid material.

In step 130, the activated cartridge from step 120 is transferred from the activation chamber 60 to a dispensing socket 28 in the cartridge holder 22 of the dispense adapter apparatus 12. The transfer is carried out by removing the activated cartridge from the activation chamber 60, and inserting the activated cartridge within the dispensing socket 28 in the cartridge holder 22. Depending upon the fluid material used, it may be desirably to wait for a period of time after activation before carrying out subsequent steps, in order to let the fluid material to reach the certain level or amount of cure or to obtain a particular viscosity which is optimum for use.

In step 140, force or pressure is transferred from the dispensing device 12 to a plunger 40 of the dispenser adapter apparatus. As related above, the plunger 40 slidably engages a bore 42 in the cartridge holder 42. The transfer of force or pressure is generally carried out by interfacing the plunger 40 of the dispenser adapter apparatus 12 with the piston 14 of the dispensing device 12 as discussed above.

In step 150, fluid material is forced from a cartridge 30 held in the dispensing socket 28 of the cartridge holder 22. Generally, the fluid material is forced from the cartridge 30 by the action of the plunger 40 thereupon, as described above, so that material contained within the cartridge 30 may be applied for various uses.

Additional steps may also be utilized with the present invention, including the step of removing a spent cartridge from the cartridge holder apparatus, and placing a fresh cartridge within the activation chamber. The step of interchanging different dispenser adapters on the dispensing device, and the step of interchanging different dispensing devices with the same dispenser adapter, may also be included with the invention. When the invention is used with fluid materials which do not require activation, steps 120 and 130 are generally omitted from the above procedure.

As illustrated by the above embodiment of the invention, it can be seen that a variety of dispenser adapter apparatus may be used interchangeably on a single dispensing device to allow activation and dispensing of a variety of fluid materials with a single dispensing device. For example, fluid materials used in the dental profession (some of which do not require activation), such as glass ionomer compounds, resins, sealants, de-sensitizing agents, disinfecting agents, astringents, coagulants, chelating agents, amalgams, cements, porcelain cements, micro- and macro-fill composites and hybrid composites may be activated and dispensed or applied with the present invention. Thus, the invention may used for numerous dental procedures, including crowns, temporary and long-term fillings, bridgework, inlays, onlays, posts, pins, cast cores, cast crowns, orthodontic bands, and other applications. In endodontic dental applications, gutta percha may be dispensed with the invention for replacing the root or pulp material in root canal procedures. Impression materials such as polyether, alginate, rubber, silicones, hydrocolloid, polysulfite and poly vinyl siloxane, may also be dispensed by use of the present invention. Commercially available dental materials which may be dispensed with the invention include, but are not limited to, SUPERDENT™, PROTEMP™, PHOTAC-FIL™, IMPREGUM®, PENTA®, PERMADYNE®, KETAC®, MAGNACORE™, OPTIBOND™, PHOTAC™, PRISMA™, DYRACT™, REPROSIL™, NUPRO®, DELTON™, DENTHESIVE™, DURAFILL™, ULTRAFIL®, HELIOSEAL™, MIRACLE MIX™, PERTAC™, FUJI II®, TETRIC™, AQUASIL™, and TPH™. These examples are provided merely to illustrate some of the many fluid materials used in the dental profession which may be dispensed with the present invention.

The dispensing device used with the invention may be a conventional syringe as shown above, and thus dentists using the invention no longer need to purchase multiple dispensing devices for the above materials, but may use their anesthetic syringe, thereby avoiding the additional cost which has heretofore been required for purchasing multiple dispensing devices for application of different fluid materials. Thus, the invention provides a significant reduction in expense for dental professionals which reduces the cost of treatment. The present invention also eliminates the clutter associated with multiple dispensing devices which generally must be on hand for dental procedures, thereby simplifying and facilitating dental procedures.

The dispenser adapter comprising the invention, as used in the dental profession, is preferably fabricated from metal or metal alloy, or natural or man-made polymeric material or composite materials thereof which are heat-resistant, corrosion resistant, and generally resistant to wear, deterioration, and degradation as occurs with many of the currently used dispensing devices, thus allowing for long-term use of the dispenser adapter. Preferably, the cartridge holder, activation chamber housing and plunger of the dispenser adapter are cast or machined from aluminum, to provide an inexpensive dispenser adapter which is easily autoclavable or otherwise sterilizable for re-use. An anti-stick coating such as HARDCOAT™, TEFLON® or a like coating may be included on the plunger and cartridge holder surfaces to prevent adhesives or other materials used with the invention from sticking to parts of the apparatus which could otherwise cause jamming as occurs in background art dispensing devices. Anti-slip coating may be included on the exterior of the cartridge holder to facilitate handling of the invention while wearing gloves. It is alternatively contemplated that the invention may be fabricated from inexpensive polymeric materials so that the dispenser adapter comprising the invention is disposable. It is further contemplated that the cartridge holder and plunger of the invention may be fabricated from resilient or flexible materials so that the dispenser adapter may be twisted or bent during use to allow more precision in dispensing or applying materials. As shown above, the dispenser adapter may be made in various lengths to facilitate particular operations. Thus, the invention is particularly well suited to endodontic procedures wherein anesthetics and other medications must be injected with precision.

For application of fluid materials which require heating prior to their dispensation, such as gutta percha or other heat activated materials, a heating element may be included within the cartridge holder in association with the activation chamber or socket, or a heating jacket may be utilized with the cartridge holder to activate materials prior to use, and to facilitate material application generally.

In a profession such as dentistry wherein many different materials are to be dispensed and several configurations of the dispenser adapter apparatus and cartridges may be on hand, the individual dispenser adapter apparatus may be color coded for quick identification, so that time is not wasted experimenting to see which cartridge fits with a particular dispenser adapter.

While only a single structure and configuration for a dispensing device is described above in detail for use with the invention, it should be readily understood that the dispenser adapter comprising the invention can be utilized with virtually any type of dispensing device for various fluid materials in virtually any size and shape of cartridge. It is contemplated that the dispenser adapter comprising the invention may be used with gas-operated and air-operated dispensing devices as well as hand operated dispensing devices as described above. Similarly, while the descriptive examples provided above relate primarily to the field of dentistry, it is contemplated that the invention may be used in a variety of applications. For example, in building or dwelling construction, the dispenser adapter apparatus of the invention will allow the activation and dispensing of multiple adhesives, sealants, and caulks with only a single dispensing device. Likewise, in automotive manufacturing and repair, a variety of sealants, lubricants and adhesives may be dispensed with a single dispensing device through use of the invention. In medical and surgical applications, the invention may be used for administering anesthetics or other drugs which are available in cartridge or capsule form.

Accordingly, it will be seen that the present invention provides a dispenser adapter apparatus which allows various types of materials to be activated and dispensed with a single dispensing device. Although the description above contains many specificities, these should not be construed as limiting the scope of the invention but as merely providing illustrations of some of the presently preferred embodiments of this invention. Thus, the scope of the invention should be determined by the appended claims and their legal equivalents.

I claim:

1. A dispenser adapter apparatus, comprising:
   (a) a cartridge holder;
   (b) a plunger, said plunger associated with said cartridge holder;
   (c) means for transferring force from a dispensing device to said plunger;
   (d) means for activating fluid materials within a cartridge; and
   (e) means for coupling said cartridge holder to said dispensing device.

2. A dispenser adapter apparatus as recited in claim 1, wherein said cartridge holder has a first end and a second end, said cartridge holder including a socket adjacent said first end, said activating means and said coupling means included adjacent said second end.

3. A dispenser adapter apparatus as recited in claim 1, wherein said cartridge holder includes a longitudinal bore, said plunger slidably accommodated within said bore.

4. A dispenser adapter apparatus as recited in claim 1, wherein said transferring means comprises means for interfacing said plunger with a piston of said dispensing device.

5. A dispenser adapter apparatus as recited in claim 1, wherein said plunger has a first end and a second end, said first end of said plunger positioned adjacent said socket of said cartridge holder, said transferring means associated with said second end of said plunger.

6. A dispenser adapter apparatus as recited in claim 1, wherein said activating means comprises an activation chamber, said activation chamber included in said cartridge holder, said bore communicating with said activation chamber.

7. A dispenser adapter apparatus as recited in claim 1, wherein said activating means further comprises means for applying activating pressure to a cartridge by said dispensing device.

8. A dispenser adapter apparatus, comprising:
   (a) a cartridge holder, said cartridge holder including a longitudinal bore, said cartridge holder including a socket;
   (b) an elongated plunger, said plunger slidably engaging said bore in said cartridge holder;
   (c) interfacing means for transferring pressure from a dispensing device to said plunger;
   (d) an activation chamber, said activation chamber included with said cartridge holder, said bore communicating with said activation chamber;
   (e) means for applying activating pressure to a cartridge in said activation chamber by said dispensing device; and
   (f) coupling means for attaching said cartridge holder to a syringe.

9. A dispenser adapter apparatus as recited in claim 8, wherein said cartridge holder has a first end and a second end, said socket located adjacent said first end, said activation chamber and said coupling means located adjacent said second end.

10. A dispenser adapter apparatus as recited in claim 8, wherein said plunger has a first end and a second end, first end of said plunger positioned adjacent said socket of said cartridge holder, said second end of said plunger positioned adjacent said activation chamber, said interfacing means positioned adjacent said second end of said plunger.

11. A dispenser adapter apparatus as recited in claim 8, wherein said pressure applying means comprises an aperture, said aperture adjacent said second end of said cartridge holder, said aperture in communication with said activation chamber.

12. A dispenser adapter apparatus as recited in claim 11, wherein said aperture is co-linear with said bore, said aperture extending through said coupling means.

13. A dispenser adapter apparatus as recited in claim 12, wherein said aperture is structured and configured to slidably accommodate a piston of said dispensing device.

14. A dispenser adapter apparatus, comprising:
   (a) a cartridge holder, said cartridge holder having a first end, said cartridge holder having a second end, said cartridge holder including a longitudinal bore, said cartridge holder including a socket adjacent said first end, said bore communicating with said socket;
   (b) said cartridge holder including an activation chamber, said bore communicating with said activation chamber;
   (c) a plunger, said plunger slidably engaging said bore in said cartridge holder, said plunger having a first end adjacent said socket, said plunger having a second end adjacent said activation chamber;
   (d) coupling means for attaching said cartridge holder to a dispensing device, said coupling means adjacent said activation chamber, said coupling means having an aperture extending therethrough, said aperture communicating with said activation chamber;
   (e) means for applying activating pressure to a cartridge in said activation chamber by said dispensing device; and
   (f) interfacing means for transferring force from a piston in said dispensing device to said plunger.

15. A dispenser adapter apparatus as recited in claim 14, wherein said activating pressure applying means comprises an aperture, said aperture adjacent said second end of said cartridge holder, said aperture in communication with said activation chamber.

16. A dispenser adapter apparatus as recited in claim 15, wherein said aperture is co-linear with said bore and said aperture extends through said coupling means.

17. A dispenser adapter apparatus as recited in claim 16, wherein said aperture is structured and configured to slidably accommodate a piston of said dispensing device.

18. A method of dispensing fluid materials, comprising the steps of:
   (a) providing a dispenser adapter, said dispenser adapter comprising a cartridge holder, said dispenser adapter comprising a plunger slidably associated with said cartridge holder, said dispenser adapter including a socket, said dispenser adapter including an activation chamber;

(b) coupling said dispenser adapter to a dispensing device;

(c) placing a cartridge of fluid material within said activation chamber;

(d) applying an activating pressure to said cartridge in said activation chamber;

(e) transferring the activated cartridge from said activation chamber to said socket;

(f) transferring force from said dispensing device to said plunger on said dispenser adapter; and (g) forcing, by said plunger, fluid material from said cartridge in said cartridge holder.

19. A method for dispensing fluid materials as recited in claim 18, wherein said step of applying activating pressure is carried out by a piston on said dispensing device, said piston entering said activation chamber through an aperture in said cartridge holder.

20. A method for dispensing fluid materials as recited in claim 18, further comprising the steps of removing a spent cartridge from said socket and inserting a fresh cartridge in said activation chamber.

* * * * *